(12) United States Patent
Borowczak et al.

(10) Patent No.: US 6,644,122 B2
(45) Date of Patent: Nov. 11, 2003

(54) METHOD FOR ULTRASONIC MONITORING AND EVALUATING OF COMPOSITES

(75) Inventors: Marc Borowczak, North Canton, OH (US); Aaron Scott Puhala, Kent, OH (US); Ran Ding, Hudson, OH (US); Fredrick Lewis Magnus, Mogadore, OH (US); Blake Edward Matthies, Akron, OH (US)

(73) Assignee: The Goodyear Tire & Rubber Company, Akron, OH (US)

( * ) Notice: Subject to any disclaimer, the term of this patent is extended or adjusted under 35 U.S.C. 154(b) by 41 days.

(21) Appl. No.: 10/036,909

(22) Filed: Dec. 21, 2001

(65) Prior Publication Data

US 2003/0115962 A1 Jun. 26, 2003

(51) Int. Cl.$^7$ ............................................. G01N 29/20
(52) U.S. Cl. ............................ 73/602; 73/597; 73/598; 73/644
(58) Field of Search .................... 73/602, 597, 598, 73/599, 600, 628, 644, 641, 642, 643

(56) References Cited

U.S. PATENT DOCUMENTS

| | | | | |
|---|---|---|---|---|
| 3,663,842 A | * | 5/1972 | Miller ........................ | 310/338 |
| 4,238,725 A | * | 12/1980 | Karplus et al. ............ | 324/727 |
| 4,249,421 A | * | 2/1981 | Gaunaurd et al. .......... | 73/589 |
| 4,313,070 A | * | 1/1982 | Fisher ........................ | 310/313 R |
| 4,484,475 A | * | 11/1984 | Ogura et al. ............... | 73/579 |
| 4,658,649 A | * | 4/1987 | Brook ........................ | 73/624 |
| 4,674,334 A | * | 6/1987 | Chimenti et al. .......... | 73/627 |
| 5,187,980 A | * | 2/1993 | Blair et al. ................ | 73/599 |
| 5,537,876 A | * | 7/1996 | Davidson et al. .......... | 73/624 |
| 5,713,916 A | * | 2/1998 | Dias .......................... | 606/169 |
| 5,866,820 A | * | 2/1999 | Camplin et al. ........... | 73/643 |
| 5,913,243 A | * | 6/1999 | Hopeck et al. ............. | 73/644 |
| 5,992,235 A | * | 11/1999 | Fischer et al. ............. | 73/617 |
| 6,360,610 B1 | * | 3/2002 | Jarzynski et al. .......... | 73/627 |
| 6,439,034 B1 | * | 8/2002 | Farone et al. .............. | 73/54.24 |
| 6,513,385 B1 | * | 2/2003 | Han et al. .................. | 73/629 |

\* cited by examiner

*Primary Examiner*—Hezron Williams
*Assistant Examiner*—Jacques Saint-Surin
(74) *Attorney, Agent, or Firm*—David E. Wheeler; Richard B. O'Planick

(57) ABSTRACT

Ultrasonic sensors can be integrated and used to monitor composites throughout their production and during their useful lifetime. In an integrated program, ultrasonic sensors, in the illustrated embodiment contact sensors, can be used for quality control on raw rubber used for making a composite and for monitoring the cure of the rubber as it is transformed into a useful product, and non-contact sensors can be used to evaluate the product when it is completed, and to monitor its aging and wear during use. Such sensors can also be used in research to evaluate potential raw materials, and to compare cured candidate materials for properties useful in a completed product.

10 Claims, 7 Drawing Sheets

METHOD FOR ULTRASONIC MONITORING AND EVALUATING OF COMPOSITES

FIELD OF THE INVENTION

The invention relates to a method and apparatus for monitoring the production of products wherein a chemical transformation takes place during production, as well as monitoring quality control, wear, and other physical properties.

BACKGROUND OF THE INVENTION

Ultrasonic sensors, and particularly Piezo Electric sensors are used extensively in industry as warning devices, for example as a proximity sensor to detect when someone is getting too close to machinery, and as pressure sensing devices for mapping the contact pressure profile between two objects, such as Tekscan ultrasonic sensors. Characteristics of ultrasonic sensors are well recognized by those skilled in the art.

Ultrasonic sensors may comprise contact sensors, such as a shear wave transducer, or non-contact sensors, such as longitudinal wave transducers. In the prior art, when it is considered that ultrasonic sensing is needed, it has been the practice that those skilled in the art determine the kind of sensor that would give them the best results, and then use the sensor for that one, specific purpose.

SUMMARY OF THE INVENTION

A method for monitoring the state of a rubber used to make a rubber or rubber composite product at all stages of development comprises the steps of: (a) using an ultrasonic sensor comprising a shear wave transducer, using a frequency of 500 kHz to 20 MHz to monitor uncured rubber compound for deviation from a standard; (b) using said shear wave transducer having a frequency of 500 kHz to 20 MHz to monitor the state of cure the rubber in a shaped rubber product or rubber composite; and (c) using a longitudinal wave ultrasonic sensor having a frequency of 500 kHz to 20 MHz to measure the properties of cured rubber in a rubber product or rubber composite.

The method may comprise measuring viscoelastic response of a cured rubber or rubber composite at more limited frequencies such as 500 kHz to 5 MHz.

The method may comprise the step of monitoring flaw development in a composite.

In a further aspect of the invention, an apparatus for monitoring the condition of a rubber or a rubber composite comprises: (a) a contact ultrasonic sensor having a frequency of 500 kHz to 20 MHz to monitor uncured rubber compound for deviation from a standard; (b) a contact ultrasonic sensor having a frequency of 500 kHz to 20 MHz to monitor the state of cure of rubber in a shaped rubber product or rubber composite; and (c) an air coupled ultrasonic sensor having a frequency of 500 kHz to 20 MHz to measure the properties of cured rubber in a rubber product or rubber composite.

In an illustrated embodiment of the apparatus, an air medium is used for the longitudinal wave transducer.

In an illustrated embodiment, the signals of the ultrasonic sensors have a 1 MHz central frequency.

BRIEF DESCRIPTION OF THE DRAWINGS

The invention will be described by way of example and with reference to the accompanying drawings in which.

DETAILED DESCRIPTION OF THE INVENTION

In the development of the present invention, the inventors theorized that if the proper ultrasonic sensors are chosen, and are optimized for each specific step in the production of a product, or the stage in the life of a product, ultrasonic sensors could be used in a comprehensive way to monitor the development of a product during manufacture, and to provide quality control for the completed product, in addition to providing a means to monitor the changing physical properties of the product during use, such as wear and aging.

Although the present invention is illustrated with reference to rubber products, those skilled in the art will recognize that the invention can be used with any solid product that undergoes a physical, chemical, or geometric change during its manufacture. In addition, certain parts of the invention can be used independently on other types of products, for example, for testing the roughness of a finished object surface, such as sandpaper.

Figure 6:
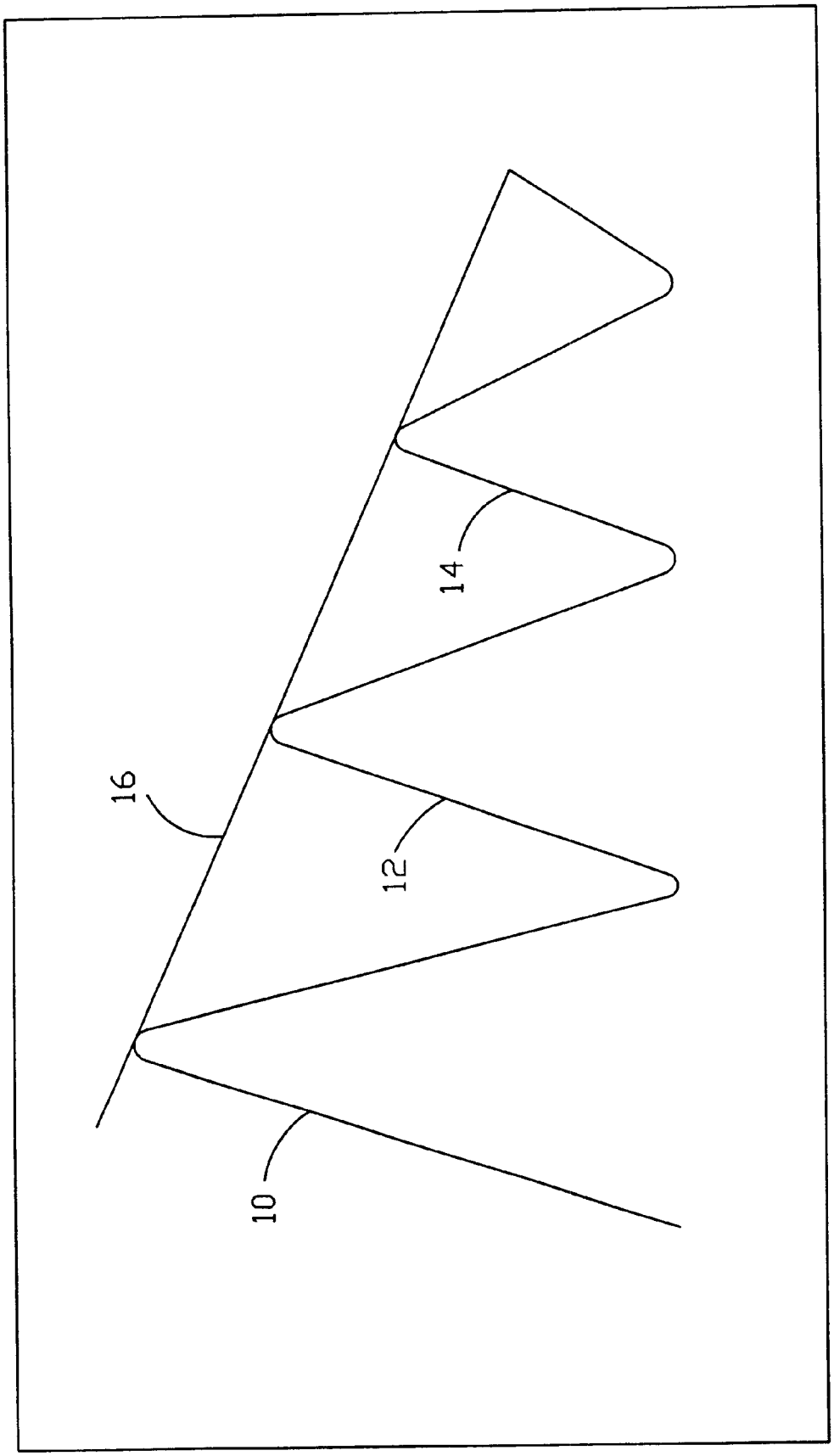
FIG. 6 illustrates the attenuation of an ultrasonic wave in a medium.

In an illustrated embodiment of the invention, a shear wave transducer (a contact sensor) is used to monitor green rubber that is used in a manufacturing process. Although, in the prior art, shear wave transducers ordinarily are used with bursts of ultrasonic energy, providing a response which can be measured, the shear wave transducer in the present invention is used by applying a chirp (a burst of ultra sound comprised of continuously varying frequency) to a sample of green rubber being tested, and the attenuation of the signal within the sample is measured (see FIG. 6). It has been found according to the present invention, that the rate of attenuation and the difference in the level of the attenuation of a signal in a rubber sample can provide a measure of the crosslink density of the rubber as well as the molecular weight of the polymers in the rubber.

Although it is believed that in other embodiments enough information may be provided by ultrasonic sensors to provide qualitative (spectral) information about materials and composites made from the materials, in the present invention the transducers are used as a quantitative tool. That is, a fingerprint of optimized raw material, treated in an optimized manufacturing process to produce an optimized product is provided, and the fingerprint of subsequent product made using the manufacturing process is compared with the established fingerprint for assurances that a quality goal is met.

Similarly, for example, when testing experimental compounds, a fingerprint of the experimental compounds can be compared with an established fingerprint for high traction compounds, high treadwear compounds, and high crosslink density compounds, in order to characterize the experimental compounds.

Figure 7:
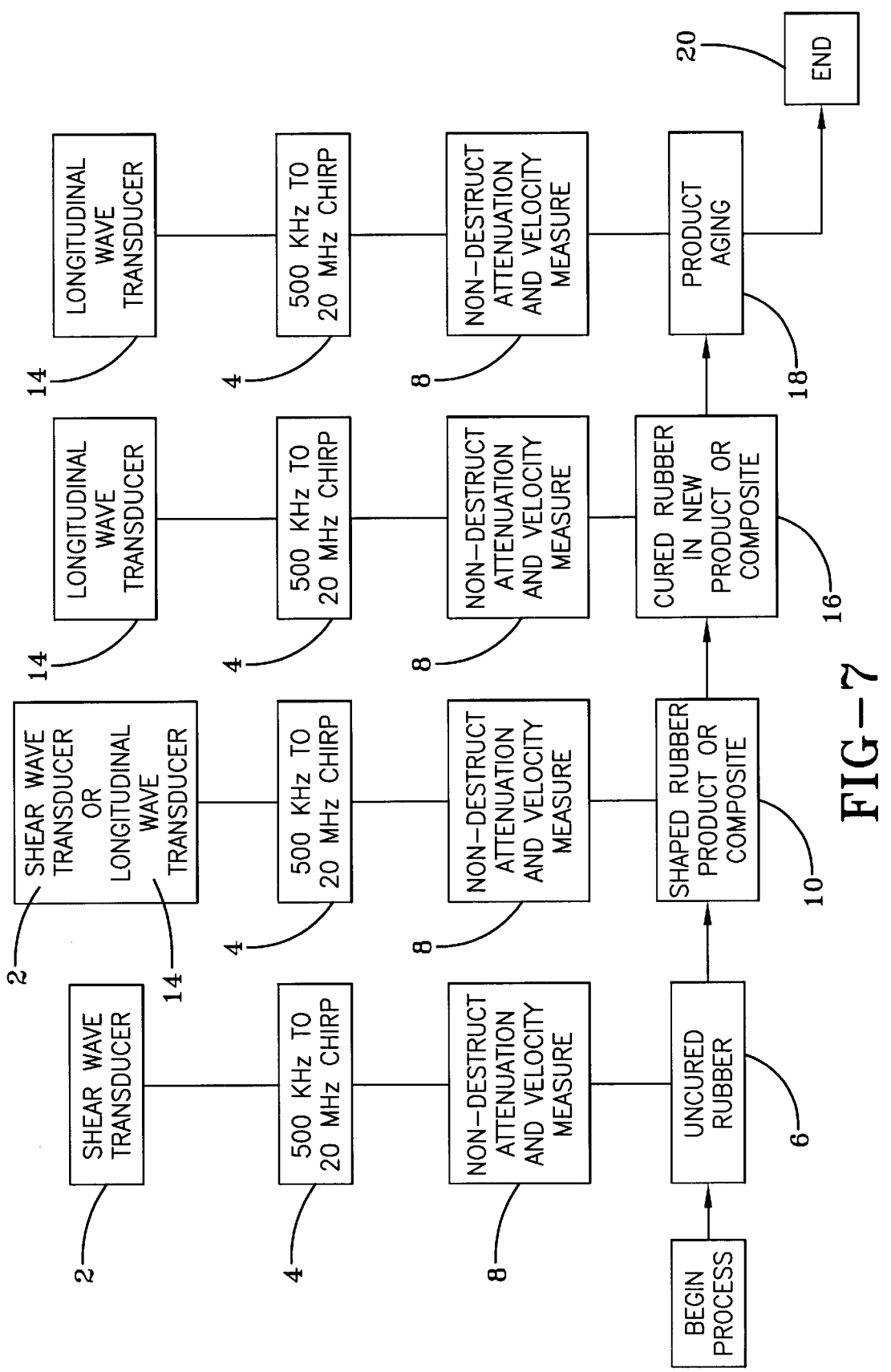
FIG. 7 illustrates in block diagram the subject method for monitoring the state of a rubber in all stages of development.

In the method of the invention, with reference to FIG. 7, a shear wave transducer (2) operates at 500 KHz to 20 MHz (4) in the form of a chirp defined herein as a burst of ultra sound comprised of continuously varying frequency. The transducer (2) is used to test green (uncured) rubber (6) in non-destructive, contact mode, manner by means of velocity and attenuation (backscatter) measurement (8). The green rubber is provided for the manufacture of a product (10) to assure the quality of the raw materials. In addition, a shear wave transducer (2) or a longitudinal wave transducer (14) can be used in like manner at 500 KHz to 20 MHz (8) in a second stage of the method in the form of a chirp signal. The transducer (2) or (14) in the second stage is used to monitor the state of cure (12) of the rubber as the manufacturing process progresses. As in stage (6), the testing of the cure rate and uncured product (10) is non-destructive and achieved by means of velocity and attenuation (backscatter) measurements. The same measurement technique is used in the subsequent stage of the method of the invention, but the longitudinal non-contact wave ultra sonic sensor (14) may be substituted in place of the shear wave transducer (2). The sensor (14) likewise operates at 500 to 20 MHz (8) by means of a chirp signal to yield non-destructive velocity and attenuation (backscatter) measurement (4) to monitor the cured rubber or surface geometry thereof in product or composite (16). The sensor (14) may further be used in an operational range of 500 to 20 Hz (8) by means of a chirp signal to yield non-destructive velocity and attenuation (backscatter) measurement (4) to monitor aging characteristics of the cured rubber or surface geometry of the product or composite throughout the product life as shown at (18), thus completing the method as indicated at (20). From the forgoing, it will be appreciated that the same methodology is thus used in each stage of the method in a non-destructive measurement of velocity and attenuation (backscatter) by different transducers (transmitter/receiver) (2) and (14).

The shear wave transducer is self-contained and is isolated from a sample being tested by a thin membrane or coating of material. To provide good contact between the transducer and the sample, a layer of coupling materials, such as honey, glycerin or other material is disposed between the transducer and the sample to provide contrast matching. By "coupling material" it is meant a material that does not significantly disrupt or hinder the signal at the interface between the sample and the transducer. Although the materials mentioned for illustration are relatively viscous materials, other less viscous materials may be used in appropriate circumstances.

Although, in the future, it may be possible to monitor the cure of a product directly, in the illustrated embodiment, plugs of sample material are cured with a product, and different plugs of material are removed and quenched during different stages of the cure. The sample plugs must be flat with parallel top and bottom sides and have a thickness of 2 mm to 8 mm, where the optimal thickness appears to be about 5 mm. When the sample is too thin, the attenuation peaks 10, 12, 14 (FIG. 6) overlap, and when the samples are too thick, the attenuation is so great that the peaks have a tendency to disappear. In the illustrated embodiment, the samples are small cylinders of material having the thickness previously indicated.

The state of the cure of the sample is indicated by the rate of attenuation of a single chirp of sound in the 500 kHz to 20 MHz range, as well as the level of attenuation.

The rate of attenuation is measured by the slope 16 (FIG. 6) obtained by comparing the ultrasonic energy transmitted in the first peak with the second and subsequent peaks of the signal obtained from the sample.

When an ultrasonic signal pulse is applied to a sample, a certain amount of the signal passes through the sample in a first wave, and a certain part of the signal is bounced off the opposing surface back into the sample. When the remaining signal bounces off the opposite surface of the sample and back to the transducer, the amplitude of the signal is reduced since a portion of its energy has already been released through the first wave. Often there are four or five such measurable waves.

The level of attenuation refers basically to the decrease in level or height of the peaks as a function of the thickness traversed by the ultrasonic energy. If there are four measurable waves in one signal and five measurable waves in a signal for a different sample, this can also be an indication of a different level of attenuation.

For its use on rubber products, it is preferred that the ultrasonic signal be provided in the frequency range of 500 kHz to 10 MHz, and in the illustrated embodiment the inventors have used a signal of 500 kHz to 3 MHz, where the center of the signal (i.e. the most efficient part) appears to be about 1 MHz.

The higher frequency limitations, e.g. 20 MHz have application in harder materials such as hard cured rubbers and rigid plastics.

After the cure is complete, the final product can further be tested using non-contact ultrasonic sensors such as longitudinal wave transducers. In the prior art, longitudinal wave transducers have been used to characterize materials using immersion techniques, i.e. a rubber sample is immersed in alcohol or water and the ultrasonic characteristics of the material are measured within such medium. In the present invention, it has been found that air can be used as a medium when proper allowances are made for humidity and temperature, when a chirp ultrasonic signal is used. It is believed, based on the information obtained using an air medium, that other gaseous media may be used when specific conditions are needed. For example, $N_2$ or another inert gas may be used if anaerobic conditions are required. Other suitable media will be apparent to those skilled in the art based on the information provided herein.

In accordance with the present invention, it has been found that there exist correlations between amplitude of attenuation and the rate of attenuation, and the traction, treadwear and crosslink density of cured rubber compounds.

It is also been found, since the signal depends to a large extent on the surface of the sample, that the scattering of the signal on rough samples can be used as a gauge of the roughness of a material. For example, once the signal for grit sandpaper is known, such a signal can be used as quality control in producing or manufacturing 40 grit sandpaper.

As the invention is applied particularly to rubber products, the invention can be used to measure the roughness of a tread surface, to measure first, how the roughness of the tread of a new tire affects traction, and second, as a measure of how the tire wears, i.e. the change in roughness of the surface during the life of a tire can be gauged.

When used for measuring the roughness of a surface, it is believed that the smallest beam that can be used to obtain meaningful results when measuring the roughness of a tread rubber is about 1 mm. In an illustrated embodiment a 6 mm beam has been used, which provides a resolution nominally of about 3 mm in a tread rubber.

Although a beam of ultrasonic energy is sometimes initiated in a tube having a specific diameter, for the purposes of measuring roughness, beam size refers to wave length, i.e. the distance between the sound waves in the beam. What this means is that, in an asperity in the tread, if a low spot or high spot varies from the average surface of the tread by 2 mm when resolution on a signal is 3 mm, the asperity will not be detected.

The apparatus of the invention has also been used to find areas of delamination in a composite product, i.e. regions in the product where the various layers have not bonded properly or completely or have debonded. Not only is it possible to find a delamination by attenuation that indicates an air bubble, it is also possible to locate the position of the air bubble. This is done by obtaining ultrasonic signals from both sides of the product. In a tire, a signal may be initiated in a tread or in the innerliner. Because the signal is attenuated differently when an air bubble is ½ inch from the surface and when it is 1 inch from the surface, a comparison of the two signals makes it possible to locate the position of the delamination precisely.

The invention is further illustrated with reference to the following example.

EXAMPLE 1

The object of this Example is to determine the correlation between high frequency ultrasonic attenuation and tire performance data obtained in passenger tire tread compound studies.

Previous testing by Goodyear indicated that ultrasonic attenuation correlates well with such tire performance variables as wet and snow traction, and as such may have some utility as a predictive tool. After the installation and testing of a NCA1000 non-contact ultrasonic tester from Second-Wave Systems, Boalsburg, Pa. was completed, the ultrasonic attenuation of 36 test tread compounds was measured. All the measurements were performed at room temperature, in transmission mode, at a frequency of 1.85 MHz. The difference in the integrated response between the first and second transmitted peaks was determined. The differential integrated response ($\Delta IR$) (also known as "the change in Integrated Response signal 11) was then compared to various previously obtained tire testing results.

Good correlations between ultrasonic attenuation at 1.85 MHz and tire performance data on wet handling, 20,000 mile wear, and snow traction were obtained with correlation coefficients ($R^2$) ranging from 0.68 to 0.74.

There are currently only a few measured compound properties which adequately and repeatably predict tire performance such as wet and snow traction. The difficulty in finding such properties was illustrated when Goodyear attempted to correlate the low-temperature shear modulus (−20° C. and 1% strain at 10 Hz) with snow traction. The resulting $R^2$ of the fit of the data obtained was relatively low (0.44), indicating that very little of the data is explained by the fit. Additionally, the uncertainty in the slope of the fit was nearly 50%.

Previous testing has shown that ultrasonic attenuation of tread compounds correlates well with wet traction. It has been suggested that the wet skid resistance of a tire (i.e. wet traction) is the result of dynamic mechanical losses at high frequencies ($\sim 10^3$–$10^6$ Hz) (G Heinrich, N Renner, and H Dummler, Kautsch. Gummi Kunstat. 49, 32, 1996).

These frequencies can increase by as much as three orders of magnitude when ABS systems are involved (Yu, B Chernak, and A I Leonov, Wear 108, 105, 1986). Rather than measuring material properties at low temperature and invoking William-Landel-Ferry (WLF) time-temperature superposition, it would be desirable to directly measure the loss properties of rubber compounds at high frequency.

One purpose of the present example was to measure the ultrasonic attenuation of tread compounds with a NCA1000 non-contact ultrasonic tester, and compare the results with previous data obtained via an immersion (ultrasonic) technique, and to also verify the correlations that were previously observed. The non-contact ultrasonic instrument typically reports $\Delta IR$, i.e. "the change in the integrated response" as a function of distance traveled through a single specimen. While not strictly an attenuation coefficient, it is a measure of the ultrasonic attenuation, assessed over a broad frequency spectrum.

Results

Figure 1:
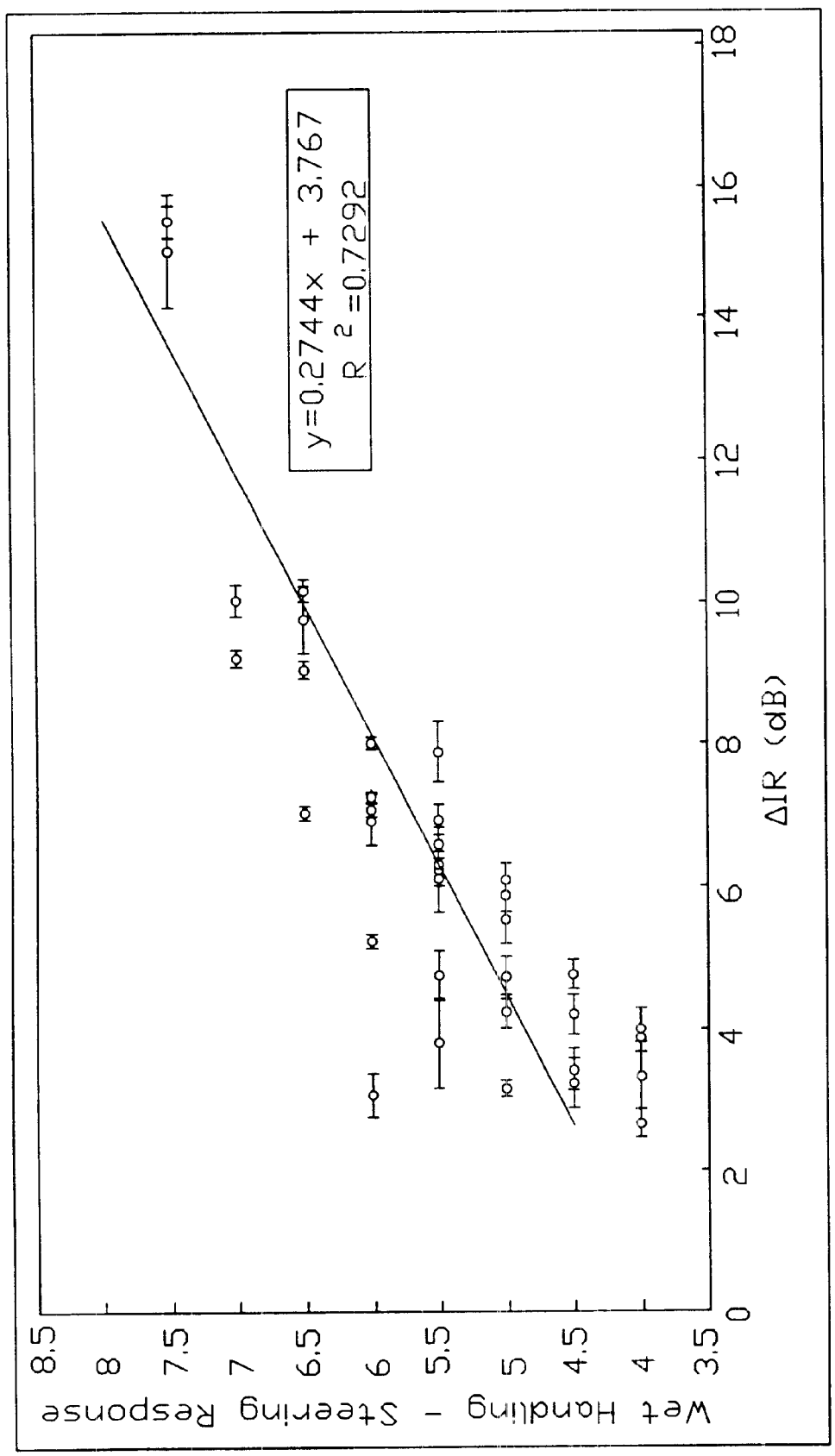
FIG. 1 shows a graphical comparison between a longitudinal attenuation coefficient and ΔIR.

FIG. 1 shows the comparison between the (Goodyear-measured) non-contact $\Delta IR$ and the longitudinal attenuation coefficient obtained previously by the immersion technique.

With an $R^2$ of 0.86, the data compare quite well. It should be noted that the immersion data was obtained on many samples of varying thickness, so the degree of cure may not be constant from sample to sample, whereas the non-contact data were obtained from a single sample. These differences may contribute to some of the observed scatter. Based on the observed correlation, one would expect that since the ultrasonic immersion data correlated well with wet and snow traction, the non-contact ultrasonic data should correlate as well.

Figure 2:
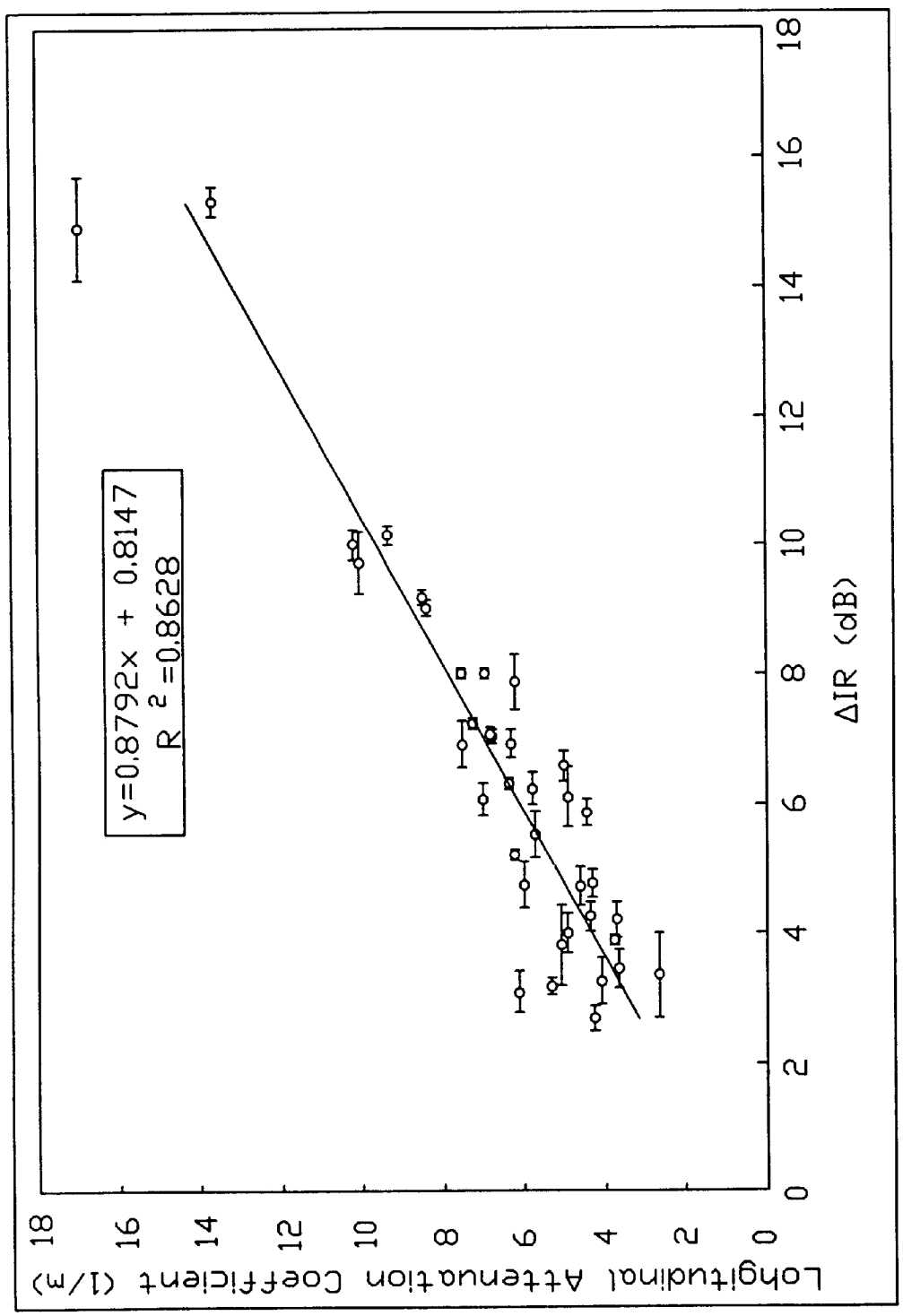
FIG. 2 shows a graphical comparison between subjective wet handling and ΔIR.

FIG. 2 shows the subjective wet handling ratings (steering response) from the same compounds as a function of $\Delta IR$.

Similar results have been obtained for other categories of subjective wet handling as well. Table 1 lists the categories and the associated $R^2$ when fit, as a function of $\Delta IR$, ranked from high $R^2$ to low $R^2$.

TABLE 1

Subjective wet handling categories and the associated $R^2$ when fit as a function of $\Delta IR$.

| Subjective Wet Handling | $R^2$ |
|---|---|
| Steering Response | 0.73 |
| Off-Throttle Under-steer | 0.73 |
| Lateral Grip | 0.70 |
| Calculated Rating | 0.70 |
| Braking Traction | 0.69 |
| Power On Under-steer | 0.68 |
| Acceleration Traction | 0.67 |
| Average Lap Time | 0.28 |
| Lateral Hydroplaning | 0.10 |
| Traction Transition | 0.09 |
| Off-Throttle Over-steer | 0.07 |
| Over-steer | 0.06 |
| Straight Line Hydroplaning | 0 |

It was noted that for the categories with particularly low $R^2$ values, the total variation in the testing results was usually around 1 rating unit, implying that these tread compounds (or the choice of tread pattern) had little or no effect on, for example, lateral hydroplaning.

Attempts were also made to correlate the ultrasonic attenuation to subjective dry handling and trailer traction data.

Figure 3:
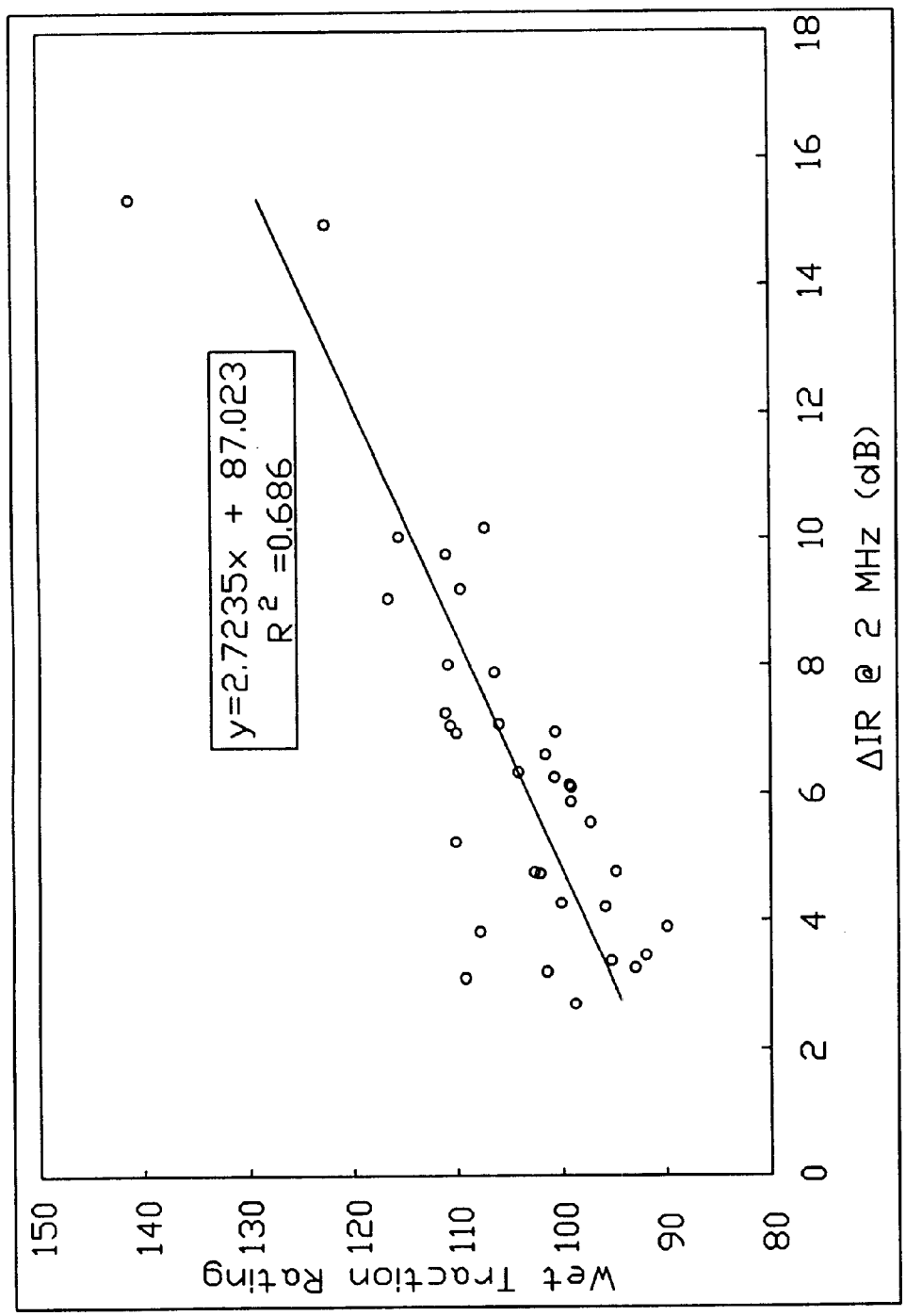
FIG. 3 shows a graphical comparison of traction trailer data and ultrasonic data on a tread compound.

The ultrasonic attenuation measured on the NCA1000 was compared with traction trailer data under wet conditions. FIG. 3 shows the comparison between traction trailer data (20 mph peak on Macadam) and subjective wet handling (braking response).

Figure 4:
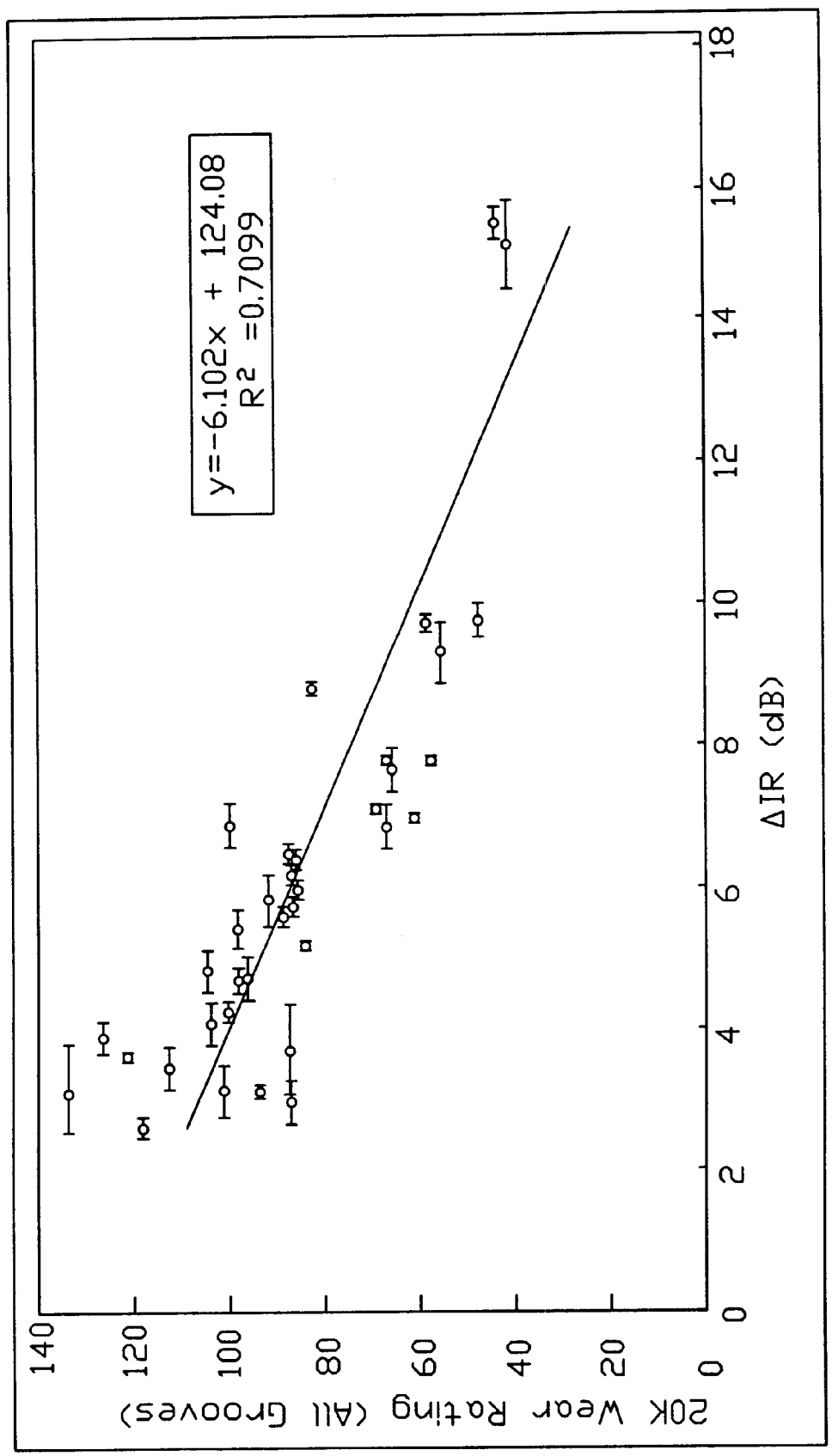
FIG. 4 shows a graphical comparison between wear rating and ΔIR

In addition to good correlations between some of the subjective wet handling categories and the ultrasonic attenuation, we have also observed good correlations between the ultrasonic attenuation and 20,000 mile wear testing with the highest $R^2$ being 0.71 (for the rear all groove average). FIG. 4 shows this data graphically.

It was observed that an exponential decay provides a better fit to the data ($R^2$=0.79), although the reason is not understood at this time. Table 2 lists the treadwear results.

TABLE 2

| 20,000 mile wear categories and the associated $R^2$ when fit as a function of ΔIR. | |
|---|---|
| 20,000 Mile Wear | $R^2$ |
| Fast Wearing Groove - Front | 0.48 |
| Fast Wearing Groove - Rear | 0.62 |
| Average Grooves - Front | 0.57 |
| Average Grooves - Rear | 0.71 |

There appears to be a better trend with the higher $R^2$ values associated with the rear tires. It would seem that this may be a result of the fact that front tires generally see higher severity than the rear tires, resulting in a different wear mechanism (i.e. high strain versus low strain). Since the ultrasonic testing is a very low-strain measurement, we may not expect much correlation to a high strain mechanism.

Figure 5:
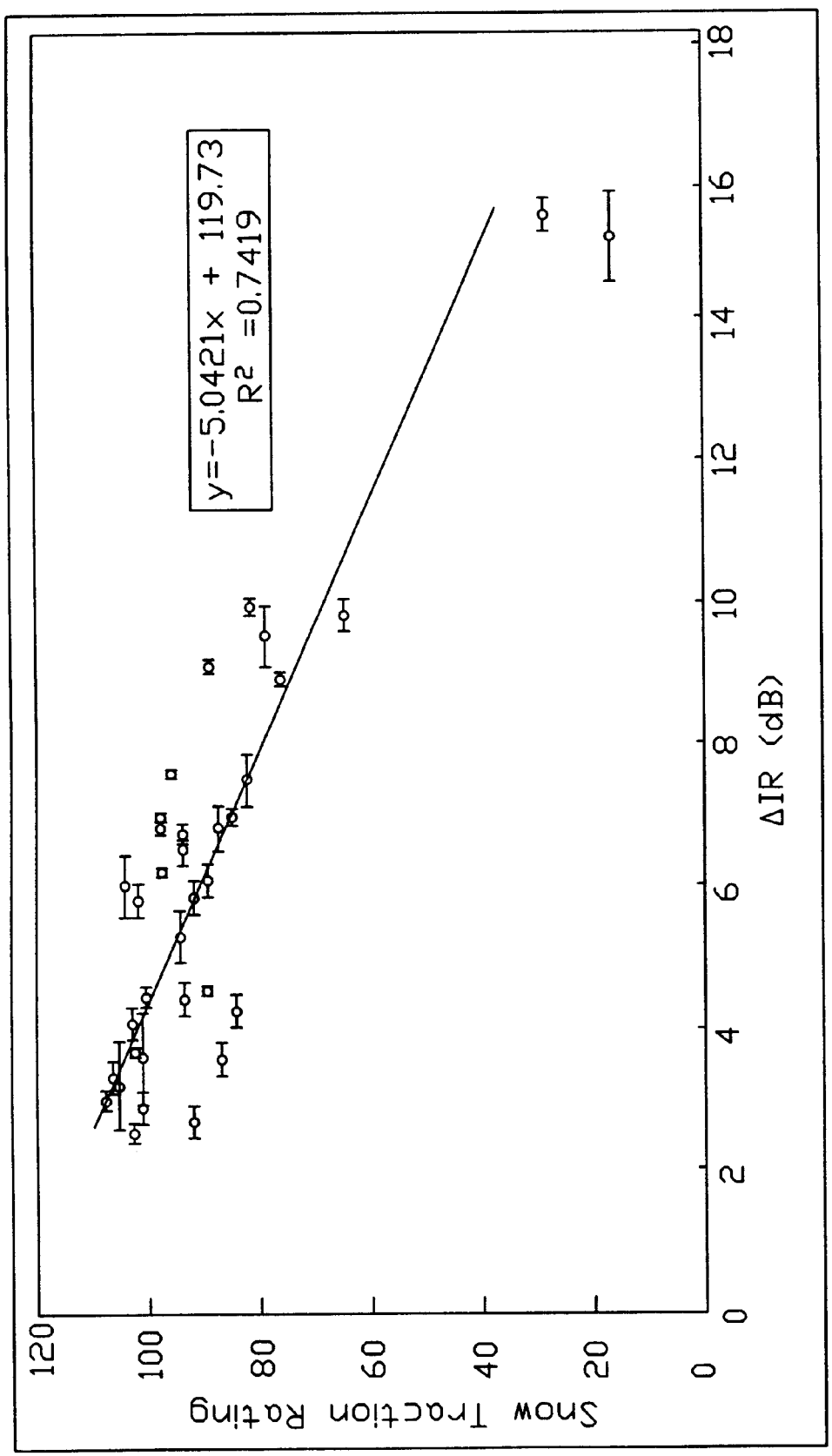
FIG. 5 shows a graphical comparison of snow traction ratings and ΔIR.

Finally, the non-contact ultrasonic attenuation and snow traction data were compared and are shown in FIG. 5.

It has been suggested that the maximum possible $R^2$ for this snow traction data is 0.78 due to the inherent variation in the testing. On this premise, it appears that the ultrasonic attenuation has great potential to assist in the prediction of snow traction. It should be noted that the particular tire performance data shown above were not chosen at random. In order to obtain some direction, all of the data were examined using scatter plot matrices to determine the most suitable candidates for more in-depth study.

Some relatively good correlations between the non-contact ultrasonic attenuation and tire performance exist, particularly ultrasonic attenuation at 1.85 MHz for such tire performance as wet handling, 20,000 mile wear, and snow traction with $R^2$ ranging from 0.68 to 0.74. These correlations indicate potential for using ultrasonic attenuation as a predictive tool.

While certain representative embodiments and details have been shown for the purpose of illustrating the subject invention, it will be apparent to those skilled in this art that various changes and modifications can be made therein without departing from the scope of the subject invention.

What is claimed is:

1. A method for monitoring the state of a rubber used to make a rubber or rubber composite product at all stages of development comprising the steps of:
   (a) using an ultrasonic sensor comprising a shear wave transducer in a first stage of the method, using a frequency of 500 kHz to 20 MHz to monitor in a nondestructive manner the attenuation of an ultrasound wave in an uncured rubber compound for deviation from a standard;
   (b) using said shear wave transducer having a frequency of 500 kHz to 20 MHz in a second stage of the method to monitor in a nondestructive manner the attenuation in an ultrasound wave the state of cure the rubber in a shaped rubber product or rubber composite, and
   (c) using a longitudinal wave ultrasonic sensor having a frequency of 500 kHz to 20 MHz in a third stage of the method to measure in a nondestructive manner the attenuation of an ultrasound wave to derive properties of cured rubber in a rubber product or rubber composite.

2. The method of claim 1 wherein step (c) may comprise the further step of measuring viscoelastic response of a cured rubber or rubber composite at frequencies of 500 kHz to 5 MHz.

3. The method of claim 1 wherein step (c) comprises the further step of monitoring flaw development in a composite.

4. The method of claim 1 wherein step (c) comprises the further steps: positioning the sensor to into a proximal relationship with the rubber product or rubber composite; and using ambient air separating the longitudinal wave ultrasonic sensor from the rubber product or rubber composite as an air medium for the propagation of the longitudinal wave.

5. The method of claim 1 wherein comprising the further step of positioning the longitudinal wave ultrasonic sensor into a proximal, non-contacting relationship with the uncured rubber compound, the uncured rubber product or composite, and the cured rubber product or composite, respectively.

6. The method of claim 5, wherein comprising the further step of using ambient air separating the longitudinal wave ultrasonic sensor from the rubber product or rubber composite as an air medium for the propagation of the longitudinal wave.

7. The method of claim 1, wherein comprising the further step of using a relatively broad band pulse chirp comprising a burst of ultrasound of continuously varying frequency from the shear wave transducer to probe the uncured rubber compound for deviation from the standard.

8. The method of claim 1, wherein comprising the further step of using a relatively broad band pulse chirp comprising a burst of ultrasound of continuously varying frequency from the shear wave transducer to probe the state of cure of the rubber in the shaped rubber product or rubber composite.

9. The method of claim 1, wherein comprising the further step of using a relatively broad band pulse chirp comprising a burst of ultrasound of continuously varying frequency from the longitudinal wave ultrasonic sensor to probe the properties of cured rubber in the rubber product or rubber composite.

10. The method of claim 1, wherein comprising the further step of using a relatively broad band pulse chirp comprising a burst of ultrasound of continuously varying frequency from the shear wave transducer and the longitudinal wave ultrasonic sensor within each stage for monitoring the uncured rubber, the shaped rubber product or rubber composite.

* * * * *